United States Patent [19]

Lee et al.

[11] Patent Number: 5,338,887

[45] Date of Patent: Aug. 16, 1994

[54] PROCESS FOR THE PREPARATION OF DIHYDROPEROXYALKYL POLYPHENYLS AND DIHYDROXY POLYPHENYLS

[75] Inventors: Guo-shuh J. Lee; Kenneth A. Burdett, both of Midland, Mich.

[73] Assignee: The Dow Chemical Company, Midland, Mich.

[21] Appl. No.: 858,465

[22] Filed: Nov. 6, 1991

Related U.S. Application Data

[63] Continuation of Ser. No. 343,473, Apr. 26, 1989, abandoned.

[51] Int. Cl.$^5$ .......................................... C07C 409/08
[52] U.S. Cl. .................................... 568/564; 568/567; 568/568
[58] Field of Search .................. 568/564, 567, 568

[56] References Cited

U.S. PATENT DOCUMENTS 4,983,777  1/1991  Van Sickle .................. 568/568

FOREIGN PATENT DOCUMENTS 8803523  5/1988  World Int. Prop. O. .

Primary Examiner—José G. Dees
Assistant Examiner—B. Frazier
Attorney, Agent, or Firm—Ann K. Galbraith

[57] ABSTRACT

A process for the preparation of dihydroxy polyphenyl compounds is disclosed which comprises the simultaneous steps of (a) contacting the corresponding diisoalkyl polyphenyl compound or an oxidation intermediate thereof with oxygen under reaction conditions sufficient to form a corresponding dihydroperoxyalkyl polyphenyl compound and (b) contacting the dihydroperoxyalkyl polyphenyl compound with an acid under reaction conditions sufficient to form the corresponding dihydroxy polyphenyl compound. In addition, the intermediate dihydroperoxyalkyl polyphenyl compound is a novel compound.

9 Claims, No Drawings

PROCESS FOR THE PREPARATION OF DIHYDROPEROXYALKYL POLYPHENYLS AND DIHYDROXY POLYPHENYLS

This is a continuation of application Ser. No. 07/343,473 filed Apr. 26, 1989, now abandoned, which is hereby incorporated by reference in its entirety.

BACKGROUND OF THE INVENTION

This invention relates to a process for preparing dihydroperoxyalkyl aromatic compounds or dihydroxy aromatic compounds from the corresponding diisoalkyl aromatic compounds.

The para,para'-dialkylates (p,p'-dialkylates) of aromatic hydrocarbons, such as 4,4'-dialkylated biphenyl or 2,6'-dialkylated naphthalene, are valuable intermediates in the preparation of monomers from which thermotropic liquid crystal polymers are synthesized. Liquid crystal polymers are high molecular weight polymers which naturally exist in or can form liquid-crystal states. The liquid-crystal state is a highly anisotropic fluid state which possesses some properties of a solid and some properties of a conventional, isotropic liquid. For example, the typical liquid crystal flows like a fluid, while retaining much of the solid state molecular order. Thermotropic liquid crystals refer to those liquid crystals which are formed by the adjustment of temperature. Generally, for a molecule to possess a liquid-crystal state the molecule must be elongated and narrow, and the forces of attraction between these molecules must be strong enough for an ordered, parallel arrangement to be maintained after melting of the solid. Thus, bulky substituents positioned anywhere but on the ends of an elongated molecule will usually destroy the liquid-crystal state.

Accordingly, p,p'-disubstituted aromatic compounds are likely to exhibit liquid crystalline properties, whereas meta- and ortho-disubstituted aromatic compounds are not. Thermotropic, liquid crystal polymers find utility in the formation of ultra high-strength fibers and films. An overview of liquid crystals may be found in Kirk-Othmer *Encyclopedia of Chemical Technology*, 3rd ed., Volume 14, John Wiley & Sons, New York, N.Y., pp. 395–427.

One group of monomers from which thermotropic liquid-crystal polymers are synthesized is the p,p'-dihydroxy polynuclear aromatics. Phenol, for example, is dialkylated at the ortho positions with isobutylene, and the resulting dialkylated phenol is coupled at the para position to form 3,3'5,5'-tetra(t-butyl)-4,4'-dihydroxybiphenyl. (See U.S. Pat. No. 4,108,908.) This substituted biphenyl is dealkylated to yield p,p'-dihydroxybiphenyl, which reacts with aromatic diacids and hydroxy acids to form liquid crystal polymers. Aromatic diacids are also prepared in a multi-step process. p-Chlorotoluene, for example, is coupled to form 4,4'-dimethylbiphenyl, which is subsequently oxidized to 4,4'-biphenyldicarboxylic acid. (See U.S. Pat. No. 4,263,466.)

As illustrated in the examples hereinbefore, the syntheses of dihydroxy polynuclear aromatics and diacids require considerable effort. In view of this and other deficiencies of the aforementioned prior art processes, it is desirable to provide an alternate route for the production of dihydroxy polynuclear aromatics which will simplify the synthesis of such compounds and their derivatives.

SUMMARY OF THE INVENTION

In one aspect, this invention is a process for preparing dihydroxy polyphenyls from the corresponding diisoalkyl polyphenyl compounds comprising the steps of contacting a diisoalkyl polyphenyl compound or an oxidation intermediate thereof with oxygen under reaction conditions sufficient to form a corresponding dihydroperoxyalkyl polyphenyl compound, and contacting the dihydroperoxyalkyl polyphenyl compound with an acid under reaction conditions sufficient to form the corresponding dihydroxy polyphenyl compound. In addition, dicarbinols, or hydroperoxyalkyl-carbinols of polyphenyls formed during the oxidation step may also be converted to dihydroxy polyphenyl compounds during the acidolysis step upon the addition of hydrogen peroxide to the reaction mixture. This process is advantageously highly selective for the production of dihydroxy polyphenyls.

In a second aspect, this invention is directed to novel para,para'- dihydroperoxyalkyl polyphenyls, preferably of the following formula:

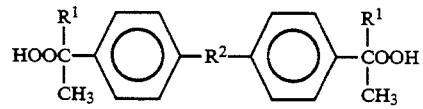

wherein $R^1$ is separately in each occurrence methyl or ethyl, and $R^2$ is phenyl, phenoxy, or a chemical bond. In a third aspect, this invention is a process for preparing para,para'-dihydroperoxyalkyl polyphenyl. These compounds are useful in the preparation of dihydroxy polyphenyls, biscarbinols, or diisopropenyl derivatives, which are useful, respectively, in the synthesis of thermotropic liquid-crystal polymers, in urethane applications, or as crosslinkers in radical polymerizations.

DETAILED DESCRIPTION OF THE INVENTION

In its first aspect, this invention is a process for the preparation of dihydroxy polyphenyl compounds which comprises the steps of:

(a) contacting a diisoalkyl polyphenyl compound or an oxidation intermediate thereof with oxygen under reaction conditions sufficient to form a corresponding dihydroperoxyalkyl polyphenyl compound, and (b) contacting the dihydroperoxyalkyl polyphenyl compound with a dissociating acid under reaction conditions sufficient to form the corresponding dihydroxy polyphenyl compound.

The term "diisoalkyl polyphenyl compounds" as used herein refers to para-substituted biphenyl, terphenyl, or para-phenoxybiphenyl compounds having two isopropyl or sec-butyl groups, or one of each, in the para positions, and are preferably compounds of the following formula:

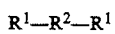

wherein $R^2$ is biphenylene, terphenylene, or para-phenoxybiphenylene, and is preferably biphenylene, and $R^1$ is independently in each occurrence isopropyl or sec-butyl and the $R^1$ groups are substituted in the para,-para' positions of the $R^2$ groups. Examples of such compounds include 4,4'-diisopropylbiphenyl compounds, 4,4'-di sec-butylbiphenyl compounds, and 4-isopropyl-4'sec-butylbiphenyl compounds. Diisoalkyl polyphenyl compounds for use in the process of this invention may be prepared by the alkylation of a polyphenyl using an acid catalyst. One example of such a method is described in copending U.S. application Ser. No. 123,741 of G. J. Lee et al., "Alkylation of Polycyclic Aromatic Compounds to Alkylates Enriched in the Para-Substituted Isomers," filed November 23, 1987, the relevant portions of which are hereby incorporated by reference.

The term "oxidation intermediate" of diisoalkyl polyphenyl compounds as used herein refers to a derivative formed by the oxidation of a diisoalkyl polyphenyl compound which forms para,para'-dihydroperoxyalkylbiphenyl, para-hydroperoxyalkyl-para'-carbinolbiphenyl, or para,para'-dicarbinolbiphenyl upon further oxidation. Examples of such intermediates include 4-isopropyl-4'-(2-hydroperoxy-2-propyl)biphenyl and 4-carbinol-4'-(2-hydroperoxy-2-propyl)biphenyl.

The oxidation step may be carried out in any suitable reaction vessel into which an oxygen-containing gas may be introduced. This step is preferably carried out with the use of essentially pure oxygen or mixtures of oxygen with inert gases, but may also be carried out with the use of solids which release oxygen under process conditions. Air is generally used as the source of oxygen according to the process of this invention. The oxidation step may be carried out at any pressure above the vapor pressure of the reaction mixture, and the oxygen partial pressure is preferably above about 5 psi, more preferably above about 20 psi, and most preferably above about 50 psi. Higher pressures increase the rate of oxidation, and upper limits on reaction pressures are advantageously determined by the pressure limitations of the process equipment. Preferably, the oxidation pressure is less than about 500 psig. The oxidation step may be carried out at any temperature which will permit or enable the oxidation of the polyphenyl compound, and is preferably above about 60° C., more preferably above about 80° C., and most preferably above about 90° C., and is preferably below about 150° C., more preferably below about 120° C., and most preferably below about 100° C. Temperatures above 80° C. are preferred in order to keep the product soluble and achieve the highest conversion possible. Temperatures below about 150° C. are preferred to avoid decomposition of the dihydroperoxyalkyl products to ketones and carbinols.

The temperature at which the oxidation step is conducted will also affect the relative amount of dihydroperoxyalkyl polyphenyl which is formed. Lower temperatures of about 80° C. will promote the formation of a higher percentage of dihydroperoxyalkyl polyphenyls. Higher temperatures of about 100° C. will lead to the formation of a mixture containing a higher percentage of dicarbinol polyphenyl or 4-hydroperoxyalkyl-4'-carbinol polyphenyl. The duration of the oxidation step is determined by the rate of oxidation and the level of conversion desired. This oxidation step is preferably carried out by passing the oxygen-containing gas through the compound being oxidized under the above-described conditions of time, temperature, and oxygen pressure.

The oxidation step may be carried out neat, but is preferably carried out in the presence of an inert solvent. The use of a solvent facilitates the oxidation step since a partially-oxidized polyphenyl compound may be a solid at reaction conditions. Any organic solvent which is not miscible with aqueous basic solutions and is reasonably stable at oxidation reaction conditions is suitable. Benzene, ortho-dichlorobenzene, methylene chloride, $C_{8-20}$ paraffins, and toluene are preferred, and benzene is the most preferred solvent. When a solvent is employed, the molar ratio of diisoalkylated polyphenyl compound:solvent will advantageously depend on the polyphenyl compound's solubility in that particular solvent. Less solvent is needed when the diisoalkylated polyphenyl compound is extremely soluble in the particular solvent, although the solvent is preferably present in amounts sufficient to prevent the precipitation of any oxidation catalysts employed. Although polyphenyl compounds may exhibit a higher degree of solubility in other solvents, benzene is the most preferred solvent because it is easily separated from the reaction mixture. When benzene is used as a solvent, it is preferably present in a polyphenyl compound:benzene weight ratio of about 1:2.

The oxidation step is also preferably carried out in the presence of a suitable amount of a basic material to neutralize acidic materials which can be formed as by-products in the oxidation reaction. Sodium hydroxide is the most preferred base in the process of the invention. When employed, the base is preferably present in a polyphenyl compound:base molar ratio in the range from about 1 to about 15, and more preferably about 2 to about 6. It is also preferable and within the scope of the invention to employ suitable oxidation initiators or catalysts, such as, for example, azo-bis-isobutyronitrile or α'-azo-bis(cyclohexane-1-carbonitrile), although the conversion of isoalkyl groups to hydroperoxide groups is self-initiating under most oxidation conditions. Other suitable oxidation catalysts are described in "Azo Catalysts", Encyclopedia of Polymer Science, 2(1), pp. 278–293 (1965), the relevant portions of which are hereby incorporated by reference. In one preferred embodiment, the initiator is para,para'-dihydroperoxyalkyl polyphenyl prepared by the oxidation step of the process of the invention.

Since the reaction is between heterogeneous phases, being between gaseous oxygen and liquid polyphenyl, suitable agitation is necessary. It is particularly important to bring the air, oxygen, or other oxygen-containing gas into intimate contact with the liquid phase. This may be effected, for example, by using high-speed stirrers, suitable nozzles, porous plates, or any combination thereof, together with sufficient oxygen pressure.

Although dihydroperoxyalkyl polyphenyls are the preferred product of the oxidation step, other dioxygenated materials may also be formed, including dicarbinol polyphenyl compounds and hydroperoxyalkyl carbinol polyphenyl compounds. The conversion of diisoalkyl polyphenyl compound to dioxygenated polyphenyl compound is preferably at least about 10 percent, more preferably at least about 20 percent, and most preferably at least about 30 percent. The selectivity to the dioxygenated polyphenyl compound is preferably at least about 80 percent, more preferably at least about 90 percent, and most preferably at least about 95 percent.

The dihydroperoxyalkyl polyphenyl or other dioxygenated polyphenyl materials may be separated from the reaction product, if so desired, by any suitable technique. In one embodiment, the crude oxidation mixture is mixed with an aromatic solvent to take up the polyphenyls, and is heated to form a two-phase mixture.

Representative substituted or unsubstituted aromatic solvents which may be used include, for example, benzene, xylene, toluene, chlorobenzene, ortho-dichlorobenzene, anisole, or mixtures thereof, with ortho-dichlorobenzene as the most preferred solvent. The amount of aromatic solvent used in this extraction will generally be from about 0.5 to about 20, preferably from about 1 to about 2 parts by weight of aromatic solvent to one part by weight of reaction mixture. Temperatures used for this extraction will generally range from about 10° C. to about 70° C., preferably from about 20° C. to about 30° C.

The organic layer, after removal, is contacted with an aqueous base under reaction conditions sufficient to extract the dihydroperoxyalkyl polyphenyl and other dioxygenated materials away from the starting materials and mono-oxygenated materials into the base layer. This extraction step is preferably conducted at temperatures less than about 90° C., and more preferably at about ambient temperatures, since higher temperatures may facilitate the decomposition of the hydroperoxide groups of any polyphenyls containing such groups to carbinols. This step may be repeated several times and the base layers combined. The organic layer, containing unoxygenated material and mono-oxygenated material, is preferably recycled as a starting material.

The aqueous base used in the extraction step can be water-soluble oxides, hydroxides, carbonates, bicarbonates, phosphates, or hydrogen phosphates of sodium, potassium, lithium, calcium, barium, strontium, or magnesium. The preferred aqueous basic material used in this extraction step is potassium hydroxide, preferably in a 10 to 30 weight percent aqueous solution, and more preferably in an about 15 weight percent aqueous solution. This relatively low concentration is preferred in order to minimize the decomposition of hydroperoxide groups present, especially at elevated temperatures. The amount of base used is preferably in a range from about 0.5 moles to about 4 moles, more preferably from about 1 mole to about 2 moles of base per mole of dihydroperoxyalkyl or dioxygenated polyphenyl compounds.

The base layers, after separation, and usually after combining, may be contacted with another solvent under conditions sufficient to extract the dihydroperoxyalkyl polyphenyl compound and other dioxygenated materials into an organic layer. This step may also be repeated several times. The organic layers may then be concentrated to yield solid dihydroperoxyalkyl polyphenyl or other dioxygenated polyphenyl compounds. The solvent used in the extraction step may be any solvent which has some degree of water solubility and is not affected by concentrated acid or hydrogen peroxide, and is preferably acetone, methyl isobutyl ketone, methyl ethyl ketone, or methylene chloride, and most preferably is acetone. The solvent is used in a volume amount which is preferably equal to the amount of base solution. Preferably, the base solution is extracted two or three times and the organic layers are combined.

The second step of the process of the invention (hereafter referred to as the "acidolysis step") comprises contacting the dihydroperoxyalkyl-, dicarbinol-, or hydroperoxyalkyl carbinol-polyphenyl compound with a dissociating acid under reaction conditions sufficient to form the corresponding dihydroxy polyphenyl compound. This acidolysis step may be carried out in any suitable reaction vessel in accordance with conventional procedures for the acidolysis of hydroperoxides using acids as described for example, in U.S. Pat. Nos. 2,626,281 and 2,628,983, the relevant portions of which are hereby incorporated by reference. In accordance with such procedures, the hydroperoxide group is decomposed at elevated temperatures, preferably above about 50° C., in the presence of a dissociating acid.

Dissociating acids which may suitably be employed in the process of the invention are any acid with a pKa equal to or less than 5.0, and is preferably a strong mineral acid such as sulfuric acid, hydrochloric acid or strong organic acids such as acetic acid, trifluoroacetic acid, or paratoluene sulfonic acid. Most preferably, the acid employed is concentrated sulfuric acid. The acid is employed in a polyphenyl compound:acid molar ratio of above about 1:3, and preferably below about 1:0.6, and is most preferably about 1:1.

The acidolysis step is preferably carried out in the presence of hydrogen peroxide in order to convert carbinol groups present to hydroperoxyalkyl groups, which may then be converted to hydroxy groups in the acidolysis step. The hydrogen peroxide is preferably present in a molar amount such that the hydrogen peroxide:carbinol functionality ratio is approximately 1:1.

The conversion of dihydroperoxyalkyl polyphenyl compound to dihydroxy polyphenyl compound is preferably at least about 90 percent, and is most preferably at least about 99 percent. The selectivity to the dihydroxy polyphenyl compound is preferably at least about 90, and is most preferably at least about 99 percent.

The dihydroxy polyphenyl compound may be separated from the reaction product by any suitable technique. In one preferred embodiment, the reaction product is neutralized with sodium bicarbonate to form an acid salt, and then filtered to remove the acid salt. These neutralization and filtration steps advantageously remove the acid catalyst from the reaction product while retaining the dihydroxy polyphenyl compound in solution in the reaction product.

In addition, the dihydroxy polyphenyl compound may be purified by any suitable technique. In one preferred embodiment, the dihydroxy polyphenyl compound is extracted from the filtered solution with potassium hydroxide, preferably in a 10 to 30 weight percent solution, and more preferably in an about 15 weight percent solution. The base layers are then combined and neutralized with an acid, preferably with a pKa of less than about 11, such as concentrated hydrochloric acid, and filtered to yield a dihydroxy polyphenyl product of typically greater than 99 percent purity, and preferably of greater than 99.9 percent purity.

As mentioned above with respect to the oxidation step, the unoxygenated and mono-oxygenated materials are preferably recycled as starting material after the dioxygenated materials are extracted using a basic material. When the unoxygenated material and mono-oxygenated material is recycled, the process of the invention is advantageously more efficient. When the oxidation step of the process is more selective to dihydroperoxyalkyl polyphenyls, less hydrogen peroxide is needed in the acidolysis step to convert dicarbinol polyphenyls to dihydroperoxyalkyl polyphenyls. However, oxidation reaction conditions which are more selective to dihydroperoxyalkyl polyphenyls give a lower conversion of oxidation starting material. Using this extra recycling step allows the oxidation process to be conducted economically under more selective conditions, since the unconverted starting material is not discarded as waste after separation. Further, the lower percentage of dicarbinol polyphenyls in the starting material for the acidolysis step means that less hydrogen peroxide is required in that step to convert all of the dicarbinol groups to hydroperoxide alkyl groups, which are then converted to hydroxy groups.

In a second aspect, this invention is directed to novel para,para'-dihydroperoxyalkyl polyphenyls, preferably of the following formula:

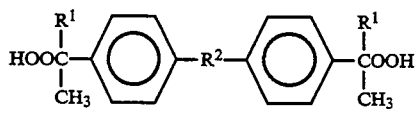

wherein $R^1$ is separately in each occurrence methyl or ethyl, and $R^2$ is phenyl, phenoxy, or a chemical bond.

In a third aspect, this invention is a process for preparing para,para'-dihydroperoxyalkyl polyphenyl. This process comprises contacting a diisoalkyl polyphenyl compound or an oxidation intermediate thereof with oxygen under reaction conditions sufficient to form the corresponding dihydroperoxyalkyl-polyphenyl compound. This process is described above as the oxidation step for the preparation of dihydroxy polyphenyls.

ILLUSTRATIVE EMBODIMENTS

The following examples are given to illustrate the invention and should not be interpreted as limiting the scope of the claims in any way. Unless stated otherwise, all parts and percentages are given by weight.

EXAMPLE 1

Preparation of 4,4'-di(2-hydroperoxy-2-propyl)biphenyl

Oxidation of 4,4'-diisopropylbiphenyl

A 100-g portion of 4,4'-diisopropylbiphenyl (DIPB) in 200 g of benzene, 200 g of 3 percent aqueous NaOH, and 1g of azo-bis-isobutyronitrile (AIBN) are loaded in a 1-liter stirred titanium reactor with 25 psig oxygen fed on demand at 80° C. for 3 days. The conversion of DIPB is about 94 percent, with 67 percent to 4,4'-di(2-hydroperoxy-2-propyl)biphenyl, 18 percent to 4-(2-hydroperoxy-2-propyl)-4'-carbinol biphenyl, and 5 percent to 4,4'-dicarbinolbiphenyl.

Purification of 4,4'-di(2-hydroperoxy-2-propyl)biphenyl

The crude oxidation mixture is dissolved in 100 g of benzene and warmed to form a two-phase mixture. The organic layer containing the dioxygenated biphenyl products is separated and is extracted twice with 35 cc portions of a 15 wt percent aqueous potassium hydroxide solution. The aqueous base layers containing the dioxygenated biphenyl materials are combined and back extracted twice with 15 cc portions of acetone. The acetone layers containing the dioxygenated biphenyl materials are combined and concentrated to yield a white solid analyzed by liquid chromatography to be 4,4'-di(2-hydroperoxy-2-propyl)biphenyl.

EXAMPLE 2

Preparation of 4,4'-dihydroxybiphenyl

Oxidation of 4,4'-Diisopropylbiphenyl

A 340 g portion of DIPB in 100 g of benzene, 200 g of 3 percent NaOH and 1 g of AIBN are loaded in a 1 l stirred titanium reactor with 50 psig oxygen fed on demand at 95° C. for 3 days. The conversion of DIPB is above about 93 percent, with 3.7 percent to 4-carbinol-4'-isopropylbiphenyl, 14.1 percent to 4-(2-hydroperoxy-2-propyl)-4'-carbinolbiphenyl, and 72.9 percent to 4,4'-dicarbinolbiphenyl.

Purification of 4,4'-Di(2-hydroperoxy-2-propyl)biphenyl

A portion of the reactor solids from Example 2 are dissolved in 100 cc of benzene and extracted three times with 65 cc of a 15 weight percent potassium hydroxide solution. Each of the base layers is back extracted twice with 60 cc of acetone. The acetone layers are combined and concentrated to give a solid product which is a mixture of the mono potassium salt of the dihydroperoxide, the hydroperoxycarbinol, and the dicarbinol. A yield of 76 percent across this step, based on the quantity of DIPB, is obtained.

Acidolysis of 4,4'-Di(2-hydroperoxy-2-propyl)biphenyl

A portion (5.0 g) of the crude oxidation solids of Example 2 containing 7.9 mmoles of difunctional equivalents are dissolved in 65 cc of acetone and brought to reflux. To this solution is added 1.79 cc of a 30 weight percent aqueous hydrogen peroxide solution. 1.3 cc of concentrated sulfuric acid (18N) is dissolved in 15 cc of cold acetone and added to the refluxing reaction mixture over 7 minutes. Reflux conditions are continued for 1 hr 25 min. The reaction product is cooled, excess sodium bicarbonate added and the mixture filtered. The acetone solution is extracted three times with 15 ml portions of 15 weight percent aqueous potassium hydroxide solution. The base layer is removed, acidified with concentrated hydrochloric acid and the resulting precipitated solids recovered by filtration, yielding 1.4 g of 4,4'-dihydroxy biphenyl as a tan solid for a 95 percent yield.

What is claimed is:

1. A dihydroperoxyalkyl polyphenyl compound of the following formula:

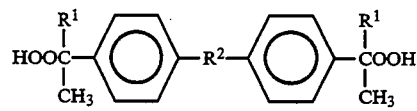

wherein $R^1$ is separately in each occurrence methyl or ethyl, and $R^2$ is phenylene or phenoxy.

2. The compound of claim 1 wherein at least one $R^1$ is ethyl.
3. The compound of claim 1 wherein at least one $R^1$ is methyl.
4. The compound of claim 1 wherein $R^2$ is phenylene.
5. The compound of claim 1 wherein $R^2$ is phenoxy.
6. The compound 4,4'-di-sec-butylbiphenyl dihydroperoxide.
7. The compound 4,4'-di-sec-butylbipenyl monohydroperoxide.
8. The compound 4-carbinol-4'-( 2-hydroperoxy-2-propyl)biphenyl.
9. The compound 4-carbinol-4'-( 2-hydroperoxy-2-butyl)biphenyl.

* * * * *